Figure 4:
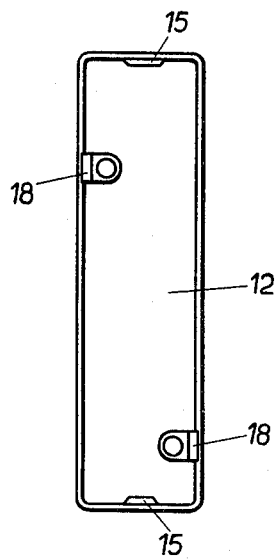
Figure 5:
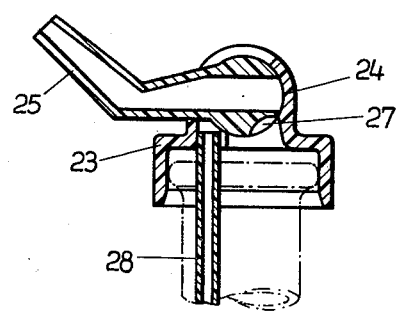

United States Patent [19]

Kruber

[11] 4,300,546

[45] Nov. 17, 1981

[54] HAND-HELD ATOMIZER ESPECIALLY FOR DISPENSING INHALATION-ADMINISTERED MEDICAMENTS

[75] Inventor: H. W. Kruber, Fachbach, Fed. Rep. of Germany

[73] Assignee: Carl Heyer GmbH Inhalationstechnik, Bad Ems, Fed. Rep. of Germany

[21] Appl. No.: 94,064

[22] Filed: Nov. 14, 1979

[30] Foreign Application Priority Data

Nov. 15, 1978 [DE] Fed. Rep. of Germany ....... 2849493

[51] Int. Cl.³ .............................................. A61M 11/00
[52] U.S. Cl. .............................. 128/200.16; 222/199; 222/536; 222/537; 239/102
[58] Field of Search ............... 128/200.14, 200.16, 128/200.17, 200.23; 222/199, 196, 536, 533, 537; 239/102

[56] References Cited

U.S. PATENT DOCUMENTS

| | | | |
|---|---|---|---|
| 3,116,856 | 1/1964 | Prussin et al. | 222/536 X |
| 3,209,751 | 10/1965 | Wakeman | 128/200.23 |
| 3,221,950 | 12/1965 | O'Donnell | 222/394 |
| 3,404,681 | 10/1968 | Fowler | 128/200.23 |
| 3,812,853 | 5/1974 | Crain | 128/200.17 |
| 3,873,005 | 3/1975 | Hazard | 222/536 X |
| 3,970,250 | 7/1976 | Drews | 239/102 |
| 4,119,096 | 10/1978 | Drews | 128/200.16 |

*Primary Examiner*—Henry J. Recla
*Attorney, Agent, or Firm*—Karl F. Ross

[57] ABSTRACT

A hand-held aerosol dispenser, especially for medicament in the treatment of disorders requiring inhalation such as asthma, comprises a housing formed with a receptacle for the medicament and an electrically powered ultrasonic nebulizer for atomizing the liquid medicament. The housing receives a replaceable cassette or cartridge-type battery for energizing the control circuit. The housing has a compartment for enabling easy replacement of the battery and a simply opening and closing valve, from which the mist is discharged, is provided.

8 Claims, 6 Drawing Figures

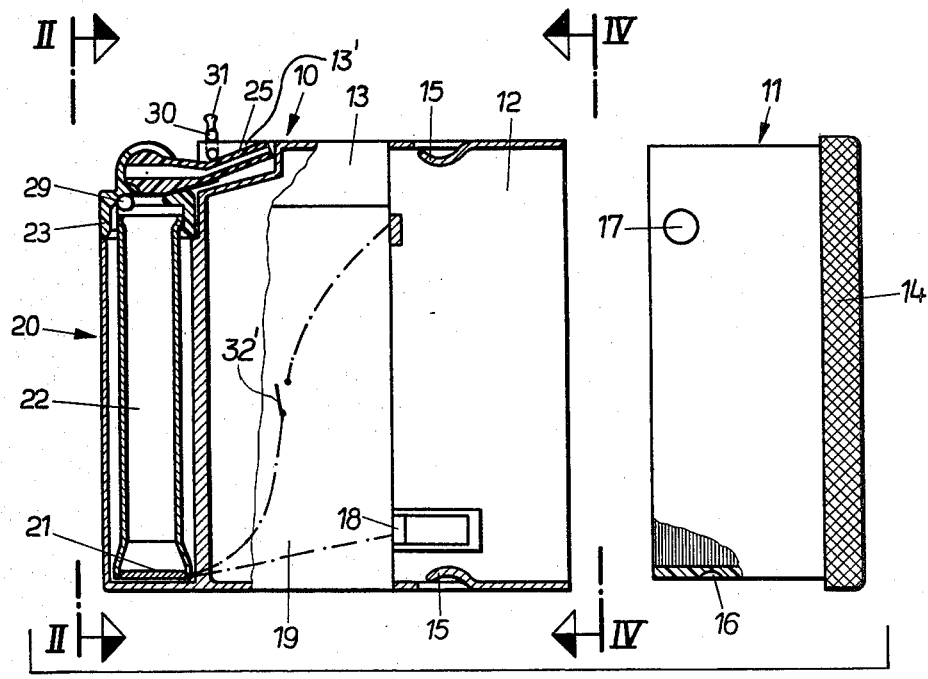

HAND-HELD ATOMIZER ESPECIALLY FOR DISPENSING INHALATION-ADMINISTERED MEDICAMENTS

FIELD OF THE INVENTION

My present invention relates to a dispenser for an atomized or nebulized liquid and, more particularly, to a hand-held dispenser for medicaments to be administered by inhalation such as those used in the treatment of asthma and in prophylaxis against asthma attacks.

BACKGROUND OF THE INVENTION

Aserosol dispensers have been provided heretofore in a wide variety of configurations for distributing or concentrating a fine mist of a liquid, such as a medicament which can be used in the treatment of illnesses responding to inhalation administration of medicaments.

In the treatment of asthma, for example, there are many liquid medicaments which are administered by inhalation techniques and are intended to be taken in by mouth or nasal inhalation to penetrate the lugs and bronchial system of the patient.

In very early technology of this type, the aerosol dispenser was usually a glass flask to which a bulb was affixed to drive a stream of air through an outlet, the medicament being drawn by, for example, venturi action into this stream, for atomization and distribution in finely divided form to produce the aerosol or mist. In more modern inhalation therapy, spray packages have been provided of small size so that they can readily be held in the hand of the user, the liquid medicament being combined in the package with a propellant usually a freon, which is retained under pressure until a button-operated valve is depressed to discharge a predetermined quantity of the aerosol or a continuous stream thereof.

While these systems have proved to be effective in carrying the medicament to the far reaches of the respiratory system, they have certain disadvantages which limited their applicability.

The inhaled propellant tends to remain as a residual gas in the lungs. It has been found, for example, that during the inhalation phase, this propellant mixes with ambient air and is drawn through the respiratory tract to the alveolae and, because of the greater density of the propellant, a portion of the propellant tends to remain when the air is exhaled during the next phase of the respiration cycle. The accumulation of the heavier propellant in the lungs of the patient has been found to be disadvantageous because it can cause damage to the lungs which, in many cases, is a defective organ in the patients who require treatment by inhalation threapy, such as asthmatics.

Modern inhalators and aerosol medicament dispensers have also been provided with spraying pumps which are actuated by the hand of the user and generally are of the plunger type. In such systems, when the patient depresses the actuating knob or button, he operates the pump to drive a portion of the liquid through an atomizing passage.

A disadvantage of the latter system is that the actuation of the device no longer is as simple as those using a readily operated valve. Furthermore, the operation of the device requires not only significant skill but also considerable effort which frequently cannot be exerted by a seriously ill patient or one in the throes of a significant asthma attack. When the device is improperly operated or operated with insufficient pressure, and frequently when the device is properly operated, the particle size of the liquid in the mist or aerosol is insufficiently fine to permit entrainment to the far reaches of the respiratory tract.

Attempts have been made to improve upon both types of systems, as described in U.S. Pat. No. 3,221,950, by connecting the aerosol valve with a guide tube or mouthpiece intended to carry the aerosol into the mouth of the user. However, when the aerosol utilizes a propellant, the disadvantages noted above result and when the aerosol generator is of the pump type, the problems of these systems are multiplied by the provision of the additional tube since the larger aerosol particles in part collect on the wall of the tube.

OBJECTS OF THE INVENTION

It is the principal object of the present invention to provide a hand-held dispenser for aerosols which will avoid the disadvantages of earlier systems and which can provide improved administration of inhalation liquids far patients requiring same.

Another object of this invention is to provide an easily operated hand-held aerosol medicament dispenser which is comfortable to hold, easily stored in the pocket of the user and can be operated without undue force or effort to provide an aerosol containing liquid particles in extremely finely divided form.

SUMMARY OF THE INVENTION

These objects and other which will become more readily apparent hereinafter are attained, in accordance with the present invention, in an aerosol dispenser in the form of a housing receiving a receptacle for the liquid to be nebulized, a readily manipulatable closure or valve sealing this receptacle in one position and permitting the discharging of the aerosol in another, an electrically powered ultrasonic nebulizer on the housing for generating the aerosol from the liquid, and a cassette or cartridge-type readily removable and replaceable electric powered source such as a battery which is connected through circuitry in the housing to the ultrasonic nebulizer.

The apparatus of the present invention thus can be provided with a readily manipulatable valve which need not sustain an elevated pressure since the aerosol is generated by ultrasonic action (vibration) without the development of an elevated pressure and the valve serves merely to seal the aerosol or liquid chamber in one position and to open a passage for the aerosol in another position. The liquid-receiving portion of the housing can have a removable cover affording access to the vessel which can contain sufficient liquid for the needs of the patient for a given period, say one day. The device is designed to enable the patient himself, without effort to introduce an appropriate quantity of the medicament. After the readily operated closure for this vessel is shut, the operator can insert the cassette-shaped battery which may also have sufficient power for a correspondingly operating duration, for example, one day, the battery being replaceable and preferably recharged, e.g. overnight. The circuitry can include a switch connected between the battery and the ultrasonic nebulizer which can be operated simultaneously with the valve or operated after the valve has been opened.

Advantageously, the housing is a flat generally rectangular structure so that it can be readily inserted in a pocket and easily held by the user, the receptacle or vessel and its discharge valve being provided at one end of the housing, while the battery is provided at the other end thereof.

This configuration allows the device to be handled most comfortably and its operation to be monitored easily. The medicament-containing phial is preferably composed of glass and is engageable by formations on the housing, preferably circumferentially. The glass vessel provides inert surfaces in contact with the medicament and is highly effective for both storage and dispensing or nebulizing the liquid.

The nebulizer portion of the housing is provided at its bottom with an ultrasonic transducer in the form of a vibrating plate, the upper end of the nebulizing compartment being formed with the readily removable closure formed with the aerosol outlet.

The opposing relationship of the ultrasonic vibrator and the aerosol outlet have been found to be most effective in generating the aerosol and facilitating use thereof in an appropriate orientation of the dispenser. The dispenser, more particularly, can be used without excessive inspection or thinking even in emergency situations by a patient who may not be fully conscious of the manipulative process required for operating the device.

The readily operated valve may be provided on a cap which can be fitted into the outlet opening of the nebulizer compartment so that, upon filling of the compartment or the vessel, this closure can be fully removed to provide a large opening. The valve is operated, however, with the cap in place for dispensing of the aerosol.

The valve is advantageously provided with an automatic opening mechanism, for example, a spring which biases the movable valve member into its "open" position, this member being engaged by a detent to retain it in its "closed" position against the force of the spring. The valve member thus jumps into its open position upon release of the detent for which a manual actuator can be provided. This arrangement seals the phial against leakage in any position of the unit so that it can be readily inserted and carried in the pocket.

According to another feature of the invention, the readily operated valve can be formed with a discharge tube or mouthpiece which can be unitary with the movable valve member and can facilitate the inhalation of the aerosol. It has been found to be advantageous, in this respect, to provide the mouthpiece with an additional passage communicating with the atmosphere and whereby air can be drawn into the mouth of the user through the liquid to be nebulized.

To avoid undesired operation of the unit it has been found to be advantageous to form the switch or the switch actuator as a recessed member in the wall of the housing with the member being shiftable with light pressure.

The power source of the present invention is a cassette-type rechargeable battery or seal which can have a rectangular parallelpipedal relationship and can be received in a socket-forming portion of the housing. The battery, as noted, can be charged when the device is not required, e.g. overnight, or the unit can be supplied with two interchangeable cassette-type batteries, one of which can be mounted in the unit for use while the other is being charged and vice versa.

BRIEF DESCRIPTION OF THE DRAWING

The above and other objects, features and advantages of the present invention will become more readily apparent from the following description, reference being made to the accompanying drawing in which:

FIG. 1 is an elevational view of an aerosol dispenser according to the invention with the end portions taken in section along line I—I of FIG. 2, and with the battery cartridge shown withdrawn from the right-hand side;

FIG. 2 is a view taken along the line II—II of FIG. 1;

FIG. 3 is a view in side elevation generally along the line III—III of FIG. 2;

FIG. 4 is a rear elevational view along the line IV—IV of FIG. 1;

FIG. 5 is a detail cross section through the closure of the instant invention in its closed position; and FIG. 6 is a view similar to FIG. 5 in the open position of the mouth.

SPECIFIC DESCRIPTION

The aerosol dispenser shown in the drawing at 10 is provided with a removable and replaceable current source 11 in the form of a cassette or cartridge-type rechargeable battery which can be inserted into the socket-forming end 12 of the housing 13 of the unit.

One end of the battery cartridge is provided with a knurled rib 14 which is on one of the cartridges exposed when the battery is fully inserted (compare FIGS. 1 and 3).

As can be seen from FIG. 3, the bead 14 forms a grip which can be readily engaged by the user to enable withdrawal of the battery and its replacement by a freshly charged one.

In order to retain the battery 11 in the housing, the socket-forming portion 12 is provided with a plurality of retaining springs 15 which may be bent from the wall materials of the socket portion inwardly, these detents 15 engaging in corresponding openings 16 on the bottom and top sides of the battery cartridge. The battery cartridge 11 is also provided with contacts 17 which can be of blade or knob configuration and constitute terminals against which spring contacts 18 of the housing bear when the battery cartridge is fully inserted.

The housing 13 is also formed with an electric circuit which has been represented diagrammatically at 19 in FIG. 1 and which connects the contacts 18 to the ultrasonic transducer or vibrating plate 21 at the bottom of the ultrasonic nebulizing chamber 20 formed at the opposite end of the housing 13.

The plate 21 is engaged by the bottom of a liquid-containing nebulizing vessel 22 in the form of a glass or plastic phial and which is closed at its upper end by a cap 23 which also closes the nebulizing chamber 20. The cap 23 can hermetically seal the latter chamber so that medicaments can be stored therein without danger for long periods, e.g. in units of daily dosage.

As can be seen from FIGS. 5 and 6, the closure cap 23 has an apron 23' which can hug the upper lip 22' of the glass phial 22 and, the upper portion of the cap being provided with a cylindrical pivot socket 24 in which the cylindrical valve member 26 is rotatable. The latter is formed on a mouthpiece 25 and is provided with a passage 26' communicating with the passage 25' of this mouthpiece. In the position shown in FIG. 5, the valve member 26 plugs the passage 26' and hence seals off the phial. This position corresponds to that shown in FIG. 1.

In the position illustrated in FIGS. 3 and 6, however, the passage 26' is unblocked and establishes communication with the interior of the nebulizing vessel 22. In this upright position of the valve member, a recess 27 in the underside of this member 26 establishes communication between an air inlet tube 28 and the ambient atmosphere so that air can be drawn into the nebulizing vessel.

For rapid opening of the valve 24–26, an opening spring 29 (FIG. 1) is provided, this spring being anchored in the cap 23–24 which receives the phial 22 and bears upon the mouthpiece 25 biasing it into the position shown in 26. The mouthpiece 25 can be held against the force of the spring in its closed position by a retaining latch 30 having an actuating pin or lug 31 which enables the latch to be drawn slightly laterally (away from the viewer in the FIG. 1 and toward the viewer in FIG. 3) to release the mouthpiece and allow it to swing into its open position out of a recess 13' formed in the top of the housing.

The switch 32' of the circuit, shown only diagrammatically in FIG. 1, is actuated by a pushbutton 32 which is shown to be slightly recessed below a cylindrical boss 33 in a lateral wall of the housing 13 so that this pushbutton can be readily actuated by a finger, e.g. the thumb, without the danger that the button will be depressed when the unit is in the user's pocket.

To operate the device, the user first inserts a charged battery 11 into the socket 12 of the housing. As has been observed previously, the unit is distributed with two such batteries which are interchangeable, one of which being charged while the other is used.

The cap 23 is withdrawn and phial 22 of the medicament is inserted or filled with the desired quantity of the liquid, the cap being composed of yieldable synthetic resin material so that it can be pressed tightly onto the phial 22 and yet readily removed therefrom. The cap is then replaced and the valve 25, 26 latched in its closed position.

Figure 6:
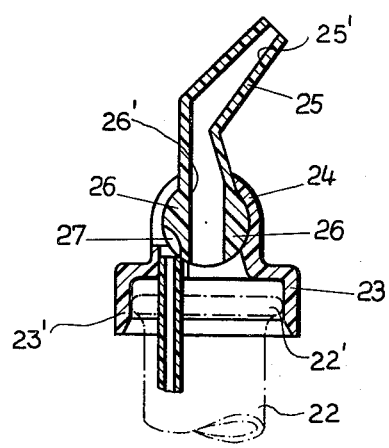

The user, as need arises, then actuates the latch 30, 31 to release the valve which presses into the position shown in FIG. 6 and inserts the mouthpiece 25 between his lips, draws a breath and simultaneously presses the pushbutton 32.

The ultrasonic transducer transforms the liquid entrained by the air drawn in by the tube 28 into an aerosol which is inhaled.

When the desired quantity of the medicament has been taken in, the pushbutton 32 is released and the valve 25, 26 again latched in its closed position. The unit can be replaced in the user's pocket and the procedure can be repeated until the vessel 22 is empty.

While the preferred and best mode embodiment of the invention provides the cartridge-shaped battery so that it fits into the back of the housing, the housing can be made to receive the cassette-type battery laterally, i.e. through an opening in one of the broad walls of the housing.

I claim:

1. A hand-held aerosol dispenser, especially for medicaments in inhalant therapy, comprising:

a housing formed with a compartment having an open upper end, receptacle means mounted in said compartment for holding a quantity of liquid to be converted into an aerosol and having an aerosol outlet;

an easily manipulated closure means mounted on said housing for covering said open upper end and for opening and closing said aerosol outlet;

an electrically operated ultrasonic nebulizer operatively associated with said receptacle means for generating an aerosol of said liquid therein;

a removable cartridge-type battery received in said housing for forming an electrical current source; and circuitry means in said housing connecting said source with said ultrasonic nebulizer, said receptacle means being a phial enclosed by a wall of said housing, said wall forming said compartment at an end of said housing remote from said battery, said closure means including a cap sealingly engaging with said open upper end of said compartment and with said open upper end of said compartment and with said aerosol outlet of said phial and having a closure member therein for opening and closing said aerosol outlet said housing being formed with a socket receiving said battery.

2. The dispenser defined in claim 1 wherein said ultrasonic nebulizer is an ultrasonic vibrating plate provided in said receptacle means at a side thereof opposite said cap.

3. The dispenser defined in claim 2 wherein said closure member in said cap is provided with said outlet passageway extending therethrough.

4. The dispenser defined in claim 3 wherein said closure member in said cap is a swingable valve member formed with said outlet passageway therethrough and displaceable between a position blocking communication between said aerosol outlet of said phial and said outlet passageway and another position opening communication between said aerosol outlet of said phial and said outlet passageway, and said dispenser further comprising means biasing said valve from said blocking position to said other position and manually operable detent means engageable with said valve for releasably retaining same in said blocking position.

5. The dispenser defined in claim 1, claim 2, claim 3 or claim 6 wherein said outlet passageway is formed with a mouthpiece receivable between the lips of the user.

6. The dispenser defined in claim 1, claim 2, claim 3 or claim 6 wherein an air inlet tube extending into said phial is provided to enable air to be drawn through said liquid.

7. The dispenser defined in claim 1, claim 2, claim 3 or claim 6 wherein said circuit means includes a switch, said housing being provided with a pushbutton for operating said switch and slightly recessed to enable storage of the dispenser in the pocket of the user without the danger of switch actuation.

8. The dispenser defined in claim 1, claim 2, claim 3 or claim 4 wherein said battery is a rechargeable battery.

* * * * *